United States Patent
Marseille et al.

(10) Patent No.: US 9,572,916 B2
(45) Date of Patent: Feb. 21, 2017

(54) PUMP, SYSTEM WITH A BLOOD PUMP AND METHOD FOR PRODUCING A BLOOD PUMP

(71) Applicant: Circulite GmbH, Aachen (DE)

(72) Inventors: Oliver Marseille, Aachen (DE); Wolfgang Kerkhoffs, Aachen (DE); Ellen Keysselitz, Aachen (DE)

(73) Assignee: CIRCULITE GMBH, Aachen (DE)

( * ) Notice: Subject to any disclaimer, the term of this patent is extended or adjusted under 35 U.S.C. 154(b) by 0 days.

(21) Appl. No.: 14/431,370

(22) PCT Filed: Sep. 25, 2013

(86) PCT No.: PCT/DE2013/000540
§ 371 (c)(1),
(2) Date: May 22, 2015

(87) PCT Pub. No.: WO2014/048411
PCT Pub. Date: Apr. 3, 2014

(65) Prior Publication Data
US 2015/0335804 A1    Nov. 26, 2015

Related U.S. Application Data

(60) Provisional application No. 61/744,693, filed on Oct. 2, 2012.

(30) Foreign Application Priority Data

Sep. 26, 2012 (DE) .................. 10 2012 018 893
Jul. 26, 2013 (DE) .................. 10 2013 012 391

(51) Int. Cl.
*A61M 1/10* (2006.01)
*A61M 1/12* (2006.01)

(52) U.S. Cl.
CPC ............ *A61M 1/1086* (2013.01); *A61M 1/122* (2014.02); *A61M 1/12* (2013.01);
(Continued)

(58) Field of Classification Search
CPC ...... A61B 5/6876; A61B 5/026; A61B 5/4836; A61B 5/686; A61B 5/6869; A61B 5/0084; A61B 5/02; A61B 5/021; A61B 5/14503; A61B 5/00; A61F 2/06; A61F 2/24; A61M 1/1086; A61M 1/122; A61M 2205/3334; A61M 2205/3375; A61M 1/10; A61M 1/12; A61M 1/125; A61M 2205/3303; A61M 2205/3331; A61N 1/3627; A61N 1/375; A61N 1/08; A61N 1/00; A61N 1/05; G06F 19/3406; G05B 23/02
See application file for complete search history.

(56) References Cited

U.S. PATENT DOCUMENTS 3,425,064 A    2/1969  Carnevale et al.
4,227,407 A   10/1980  Drost
(Continued)

OTHER PUBLICATIONS

International Search Report for Application No. PCT/DE2013/000540 mailed Apr. 7, 2014.

*Primary Examiner* — Deborah Malamud
(74) *Attorney, Agent, or Firm* — Christopher & Weisberg, P.A.

(57) ABSTRACT

The invention relates to a blood pump made of titanium with a measuring device for determining flow based on acoustic flow measurement methods, and a blood pump with a temperature sensor and/or a pressure sensor, and a system with a blood pump and an inlet cannula and/or an outlet connector and a method for producing a blood pump with a measuring device.

23 Claims, 10 Drawing Sheets

(52) U.S. Cl.
  CPC ........... *A61M 2205/3334* (2013.01); *A61M 2205/3368* (2013.01); *A61M 2205/3375* (2013.01); *A61M 2230/04* (2013.01)

(56) References Cited

U.S. PATENT DOCUMENTS

| | | |
|---|---|---|
| 6,293,901 B1 * | 9/2001 | Prem .................. A61M 1/101 600/16 |
| 7,264,606 B2 | 9/2007 | Jarvik et al. |
| 2008/0133006 A1 | 6/2008 | Crosby et al. |
| 2009/0064755 A1 | 3/2009 | Fleischli et al. |

* cited by examiner

PUMP, SYSTEM WITH A BLOOD PUMP AND METHOD FOR PRODUCING A BLOOD PUMP

The invention relates to a blood pump made of titanium with a measuring device for to determine the flow based on acoustic flow measurement processes as well as a blood pump with a temperature sensor and/or a pressure sensor as well as a system with a blood pump and an inlet cannula and/or an outlet cannula with an outlet connector as well as a procedure to produce a blood pump with a measurement device.

The task of this invention is to improve current state-of-the-art blood pumps.

This is, in accordance with the first aspect of the invention, a titanium blood pump with a measurement device to determine flow, based on acoustic flow measurement processes, whereby the measurement device has a measurement path with two coupling wedges with two transducers arranged with them, and the measurement device on a blood pump is arranged in such a way that an installation functions as a reflector.

An installation is any component that is arranged inside the pump. Any installation can be used as a reflector, so that the measurement device can be freely located on the blood pump. In particular, no space free of installations must be found for the measurement. This allows a more compact design.

Acoustic flow measurement techniques permit the determination of the flow of fluids through analysis of the flow of modulated acoustic waves. In a paired sensor unit consisting transducers acting as alternating transmitters and receivers, it can principally assess the relative transit time differences (in and against the flow direction), beam deflection (shunting) and changes in phase, amplitude and frequency of the acoustic waves. Also, scattering effects can be evaluated. So effects, such as Doppler effects or entrainment effects can be determined. A preferred embodiment is to assess the relative transit time.

In order to achieve a measurement effect and to receive the transmitted sound waves, the transducers must be installed in a specific angle range to the flow. This is done by mounting on so-called coupling wedges. The coupling wedges are firmly connected to the blood pump. This is preferably carried out by appropriate cut-outs on the pump housing. A variant is the gluing or welding of coupling wedges to the desired measurement points.

It is desirable for a blood pump to be able to determine the flow or volume, without invasively accessing the flow stream. Thus it is especially preferable not to have the transducers in contact with the bloodstream.

In a blood pump, the fluid being measured is blood. The blood pump is used to support or to replace the human heart. The blood pump satisfies the requirements for fully implantable medical devices.

Due to its corrosion resistance compared to other metals, titanium is used as the biomaterial for blood pumps. Other biocompatible materials can be used in pump construction, such as ceramics like zirconium oxide.

Advantageously, the installation is a motor and flow is measured in an annular gap. It is thus possible to integrate flow measurement in the main blood pump section. This makes it possible to have a compact structure, especially integrated wire management.

It is advantageous to have several measurement paths along the circumference. This thus increases measurement accuracy. Thus various spatial arrangements for the measurement paths, such as in the direction of the main axis or crossing the main axis or in the diagonal direction are possible. Thus even complex flow patterns can be detected.

In particular, the measurement paths can be arranged on opposite sites. A maximum distance between the measuring points can be achieved. In addition, an arrangement on the pump the housing is easily possible.

It is advantageous to place a sound barrier between the coupling wedges. This can minimise the transmission directly from one coupling wedge to another. The sound is thus ideally mainly transmitted through the fluid. Also other measures can prevent direct transmission of the sound from one coupling wedge to another coupling wedge, such as through filling with a damping medium, reducing the wall thickness of the pump housing between the coupling wedges or a milling of grooving in the wall between the two coupling wedges. In particular, a combination of these measures is advantageous.

It is advantageous if the measurement device is hermetically sealed in a space via the pump environment. If the measurement device is insulated from the environment in such a manner, a design as an implantable blood pump is particularly possible.

It is advantageous if a grommet is arranged between the space and the interior of the pump. In this way, all wires can be led in the interior of the pump.

The grommet can be arranged along a longitudinal axis. Thus the the path can also show a radial skew.

A second independent aspect of the invention relates to a blood pump which has a temperature sensor. The temperature sensor can determine the temperature of the blood while the blood pump is operating. High temperatures lead to blood damage and should therefore be avoided.

A third independent aspect of the invention relates to a blood pump whereby it has an integrated pressure sensor. The pressure sensor can either be an absolute pressure sensor or a differential pressure sensor. This pressure sensor can be integrated into a pump inlet and/or pump outlet. It can gather data on pressure conditions at both these sites on the pump Through measurement at both locations, flow can determined using a stored characteristic map. In particular, a pressure sensor can be integrated in the pump inlet when the pump inlet is placed directly into the ventricle without the interposition of a cannula. Thus an arrangement of the sensor on the outside of the pump inlet makes sense in order to measure the chamber pressure.

It is particularly advantageous here to have a combination of pressure and flow sensor technology on the pump in order to derive information on thrombi, suction or recovery. Due to the connection between the pump and the sensor/cannula there is no installation at the cannula.

A fourth independent aspect of the invention relates to a blood pump which has a first pressure sensor and a second pressure sensor, whereby the first pressure sensor is arranged in such a way that it measures pressure in one heart chamber and the second pressure sensor is arranged that it measures pressure in a downstream vascular system. The heart chamber can be, for example, an atrium or a ventricle, while the downstream vascular system can be, for example, an arterial system.

A fifth independent aspect of the invention is a system consisting of a blood pump and an inlet cannula, whereby the inlet cannula has a pressure sensor and the pressure sensor is arranged particularly at the tip of the inlet cannula. This allows for separated exchange of the components of the inlet cannula and the blood pump It is advantageous if the pressure sensor on the tip of the inlet cannula is arranged on the inside and/or the outside of the tip. It is thereby possible to measure the pressure directly in the chamber if it is mounted on the outside of the cannula, whereby a sensor placed on the inside of the tip of the inlet cannula measures the pressure within the pump system. This is possible when placing the pump in the ventricle as well as in the atrium.

A further advantage is when an additional flow sensor is arranged in the system. For example, this sensor can be placed on the inlet cannula. Flow measurement is also possible in a decoupled fashion. Also placement of a flow sensor on the outlet cannula or outlet connector is possible. This flow measurement is usually easier possible, since the flow channel is relatively large. This flow sensor technology may be provided additionally to the flow sensor technology integrated into the pump, or alternatively to it.

A further independent aspect of the invention is that the outlet cannula is equipped with an outlet connector in which a pressure sensor is placed. This allows for pressure measurement at the pump outlet. The integration of the sensor in the periphery (inlet cannula, outlet cannula with an outlet connector) creates a separation of the complex technical entities of pump and sensor units. This results in risk minimisation during production. A change of the pump during treatment is not excluded. By a separating the components, one need not change the sensors.

Pressure measurement of chamber pressure as well as systemic blood pressure in the downstream vascular system provide not only monitoring of the technical system, but also makes therapeutic monitoring possible.

A final aspect of the invention relates to a procedure to produce a blood pump with a measuring device, wherein the coupling wedges are milled from the pump housing. This means that further attachment of the coupling wedges is not needed because they are automatically integrated into the pump housing. Advantageously, the coupling wedges are thereby positioned so that that a measurement occurs in the annular gap.

A further advantage is that if a coupling wedge has an enclosing wall milled from the pump housing. This has the advantage that the coupling wedges from the three spatial directions are surrounded by a wall. They are therefore protected in these three spatial directions, and the wall need not be connected with the pump housing. Thus concomitant mounting electronic components of the measurement path can be done from above.

Further, one can drill from within the walls to the inside of the pump. Later, wires can be guided in this drill hole which lead from the inside of the wall to the inside of the pump.

The drill hole can be drilled in an axial direction. Thus, the wires s can be guided sidewards or in the direction of flow.

Finally, a cover can be installed on the wall, so that the coupling wedges are hermetically sealed off from the pump environment. Thus the measurement device is sealed off from influences from the outside, and is in particular water-sealed.

Thus the cover can be welded. This would produce a lasting, sealed connection.

The invention will be explained in more detail with reference to drawings and implementation examples below. These show.

Figure 1A:
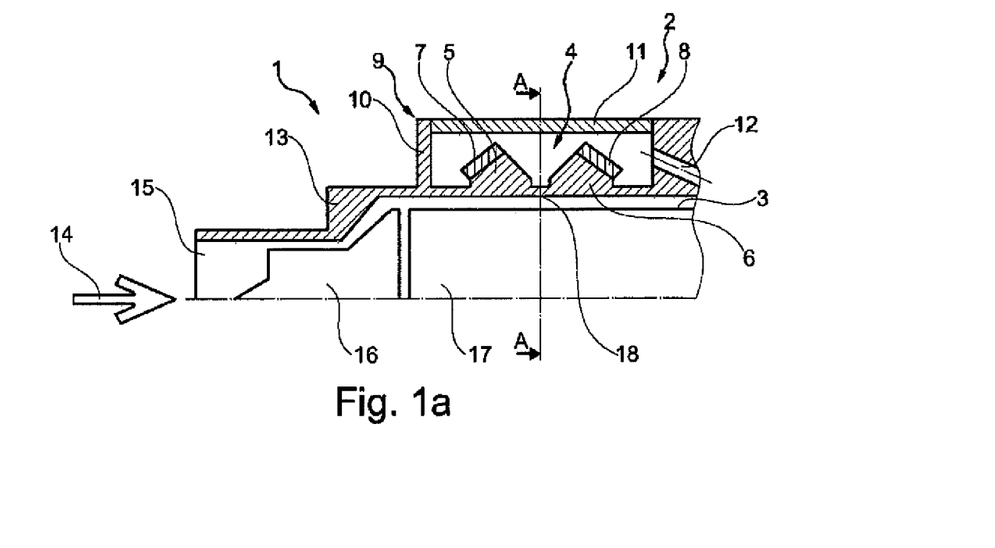
FIGS. 1a and 1b a schematic presentation of a longitudinal section through a blood pump with a measurement device and a cross-section through the blood pump with the measuring device.
Figure 1B:
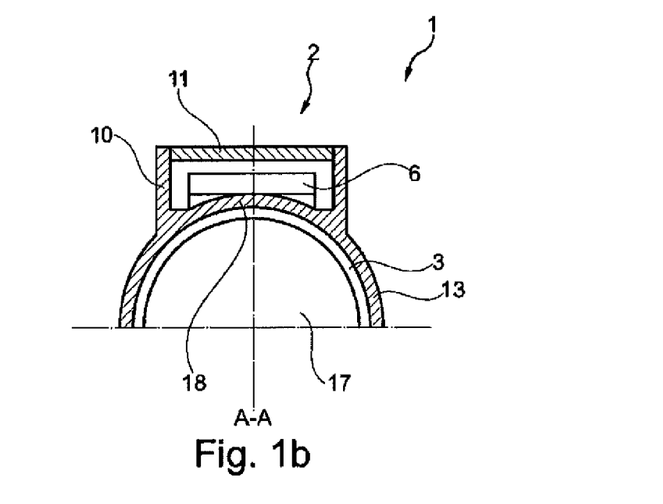

In a blood pump 1, a measurement device can be provided, as shown in FIGS. 1a and 1b, which allows for integrated flow measurement in the annular gap 3. The measuring device consists of a measuring path 4 with two coupling wedges 5, 6 and transducers 7, 8 arranged on these. The measuring apparatus 2 is arranged in a hermetically sealed box 9, consisting of a wall 10 and a cover 11. A side wall of the wall 10 has a drill hole 12, through which for operation and control of the measuring device 2 wires (not pictured) are guided sideways and to the inside of the pump.

In production, the coupling wedges 5 and 6 and the wall 10 of the box 9 are milled from the pump housing 13. Before the cover 11 is applied and sealed, the transducers 7, 8 are first welded and assembled and the appropriate wires (not pictured) for the operation and control of the transducers 7, 8 are led through the drill hole 12. Thus installation from the top is possible. Only after application and welding of the cover 11 is the flow measuring unit 2 hermetically sealed. In operation, the blood flows through the pump 1, shown schematically by the arrow 14 at the pump inlet 15 into the blood pump 1 and flows over the rotor 16 and through the annular gap 3 between the motor 17 and the pump housing 13. In order to measure the flow rate or the volume flow rate of this blood flow 14 in the annular gap, the measuring device 2 is placed for integrated flow measurement over the annular gap 3. In operation alternately the transducer 7 or the transducer 8 sends sound waves which move through the blood flow in the annular gap 3 and are reflected on the motor 17, so that the other transducer 8 or 7 receives them. From the data obtained, the flow rate or the volume flow rate can then be determined in the annular gap 3. In order to keep a direct transfer between the coupling wedges 5 and 6 as low as possible, the piece of the wall 18 of the pump housing 13 located between the coupling wedges is kept as thin as thin as possible.

Figure 2A:
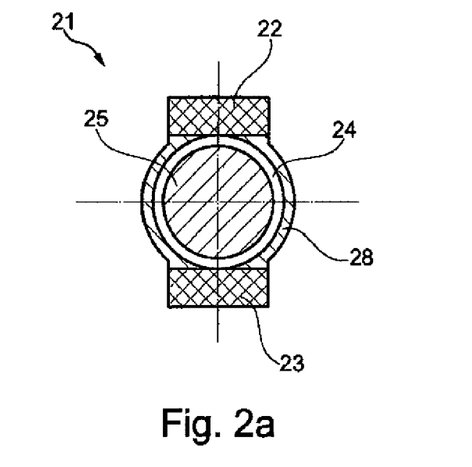
FIGS. 2a and b a schematic representation of a transverse and longitudinal section through a blood pump with a measuring device with two measuring paths, FIGS. 3a, b and c a schematic presentation of a longitudinal section through a blood pump with a measuring device, a topview of the blood pump with the measurement device and a three-dimensional side view of the blood pump with the measuring device, FIGS. 4a, b and c a schematic representation of a longitudinal section through a blood pump with a measuring device with two measuring paths, of which one has a sound barrier, a topview of the blood pump with the measuring device with two with two measuring paths of which one has a sound barrier and a three-dimensional side view of the blood pump with the measuring apparatus with two measuring paths of which one has a sound barrier, FIG. 5 a schematic representation of a cannula system with a blood pump with an inlet and an outlet cannula with an outlet connector with integrated pressure measurement at the pump inlet and outlet, FIG. 6 a schematic representation of a cannula system with a blood pump with an inlet and an outlet cannula with an outlet connector with integrated pressure measurement in the inlet cannula and an outlet connector, FIG. 7 a schematic representation of a system with a blood pump having an inlet cannula and an outlet cannula with pressure measurement integrated into the pump at the pump inlet and outlet with pressure measurement integrated in the inlet cannula and the outlet connector.
Figure 2B:
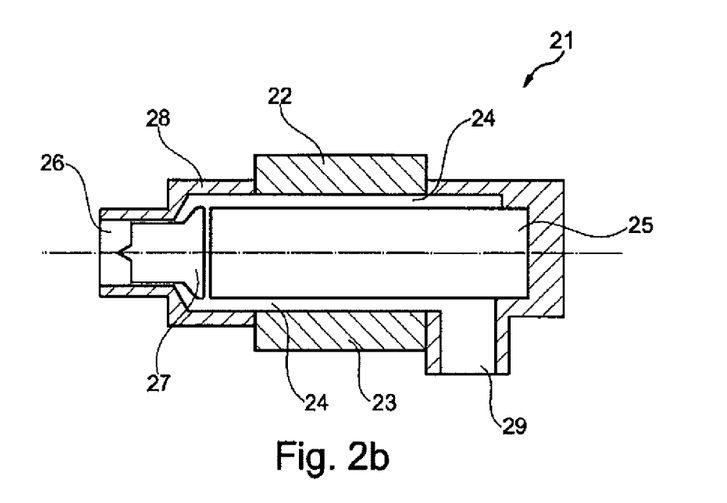

As shown in FIG. 2, a blood pump 21 can have a measuring device with several measuring paths. Thus two flow sensors 22, 23 are arranged opposite of one another to allow simultaneous flow measurement over the annular gap 24, one above the motor 25 and one below the motor 25. Also here, when operating, the blood flows through the pump inlet 26 over the rotor 27 through the annular gap 24 between the motor 25 and the pump housing 28, to then leave the blood pump 21 through the pump outlet 29. Thus the flow measurement is done by the flow sensors 22 and 23 each at annular gap 24 in which the flow is determined.

Figure 3A:
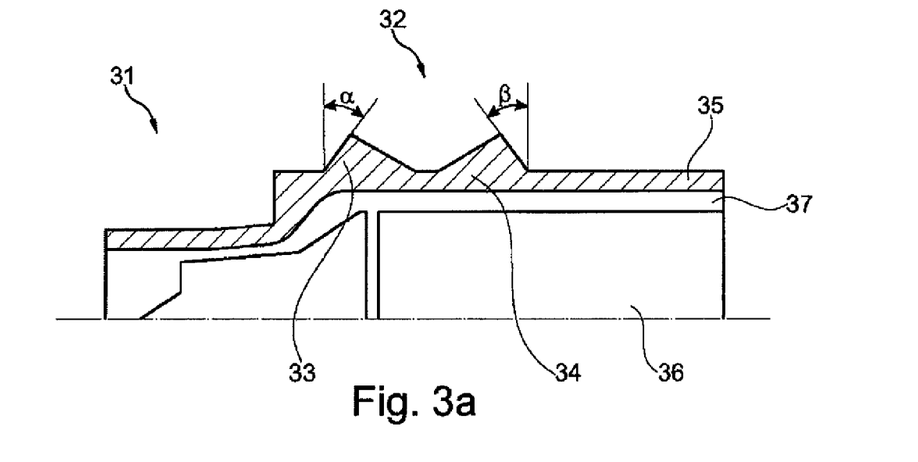
Figure 3B:
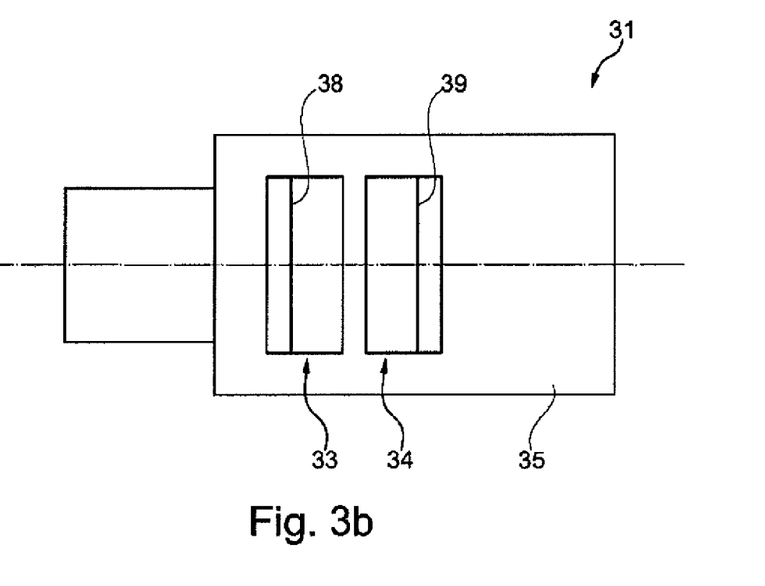
Figure 3C:
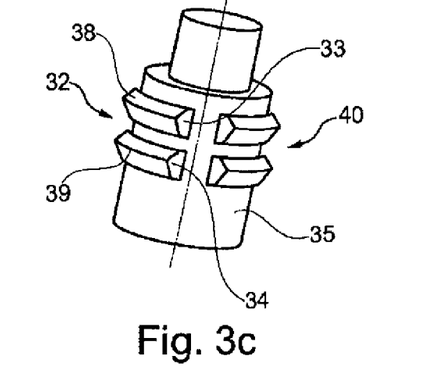

A measurement path 32 on the blood pump 31 in FIG. 3a-c, consists of two coupling wedges 33 34 which are not surrounded by a box milled from the pump housing. The measuring path 32 is positioned in axial direction. The coupling wedges 33, 34 are however again milled from the pump housing 35. The coupling wedges 33, 34 each show a coupling angle α,β of 30° perpendicular to the pump housing 35. The outside diameter of the pump housing 35 in the area of the motor 36 is about 14 mm, the inner diameter is about 11 mm, whereas the diameter of the motor itself is approximately 8.5 mm. The annular gap 37 thus has a width of about 1.25 mm. The coupling wedges 33 and 34 are arranged at a distance of about 1.8 mm and each shows in flow direction a length of 4 mm, as well as a width of 4 mm perpendicular to the flow direction. The distance between the two tips 38 and 39 of the two coupling wedges 33, 34 is approximately 7.8 mm. Offset by 90°, a second measuring path 40 is positioned with respective components.

Figure 4A:
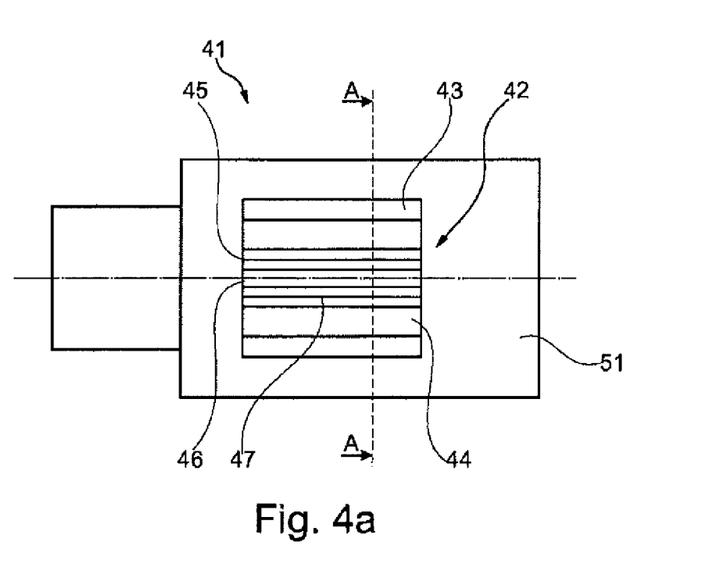
Figure 4B:
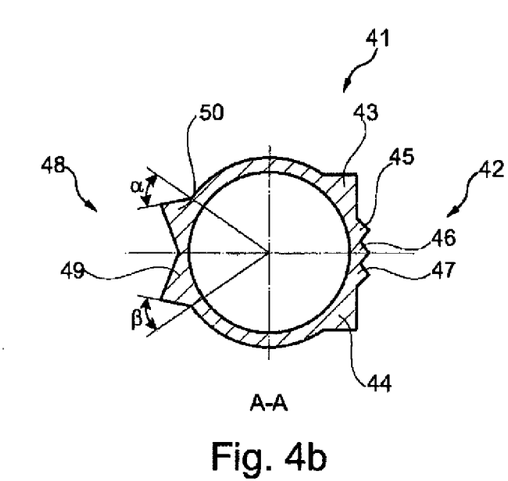
Figure 4C:
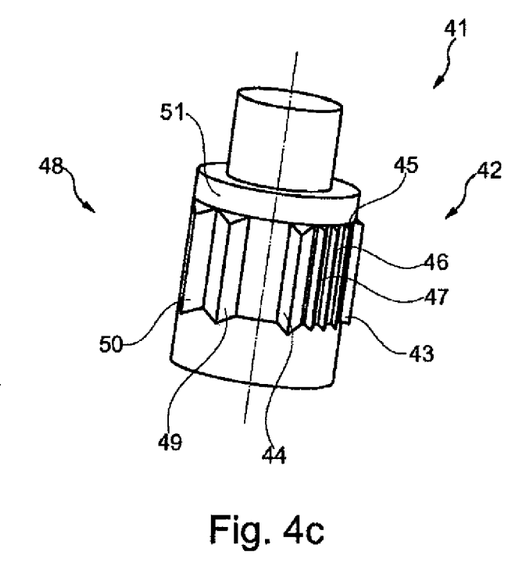

Also, on the blood pump 41 in FIG. 4a-c the measuring path 42, consisting of two coupling wedges 43 and 44 is placed in a radial orientation. This transducer has three sound walls 45, 46 and 47, which prevent transfer of sound from one coupling wedge directly to the next coupling wedge. The number of sound walls is however variable. Also a second radial measurement path 48 without acoustic breaker is provided. The coupling wedges 49 and 50 each on the outside show a coupling angle α,β of 30° to the perpendicular.

Figure 5:
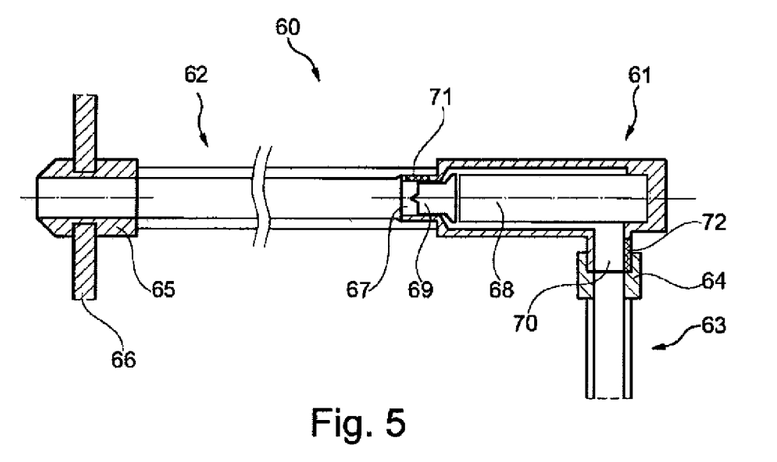

When installed a blood pump 61 is integrated into a pump system 60, see FIG. 5. Thus the pump is connected with an inlet cannula 62 and an outlet cannula with an outlet connector 63. The inlet cannula 62 is connected by a tip 65 to the heart wall 66. The blood flows over a tip 65 through the inlet cannula 62 into the pump inlet 67, where it is pumped through the motor 68 operated with the rotor 69 through the blood pump 61 to exit again at the pump outlet 70. To this, an outlet connector 64 with the outlet cannula 63 is attached. The pressure is determined at the pressure sensor 71 at the pump inlet 67 and the pressure sensor 72 at the pump outlet 70 at both these locations in the system. Thus, not only monitoring of the technical system, but also therapeutic monitoring is possible.

Figure 6:
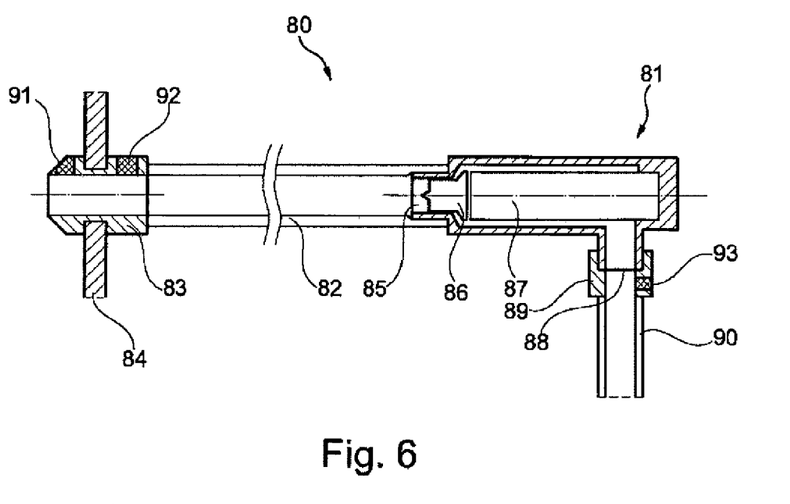

Alternatively, as shown in the blood pump system 80 in FIG. 6, the pressure can be measured at the tip 83 of the inlet cannula 82, and the outlet connector 89 of the outlet cannula 90 by the relevant sensors 91, 92 and 93. Thus sensor 91 measures the pressure distal to the heart wall 84 directly in the atrium, the sensor 92 measures the pressure within the pump system 80 at the pump inlet 85, and the sensor 93 measures the pressure within the pump system 80 at the pump outlet 88. The blood pump 81 also includes a rotor 86 and a motor 87, through which the blood is transported.

Figure 7:
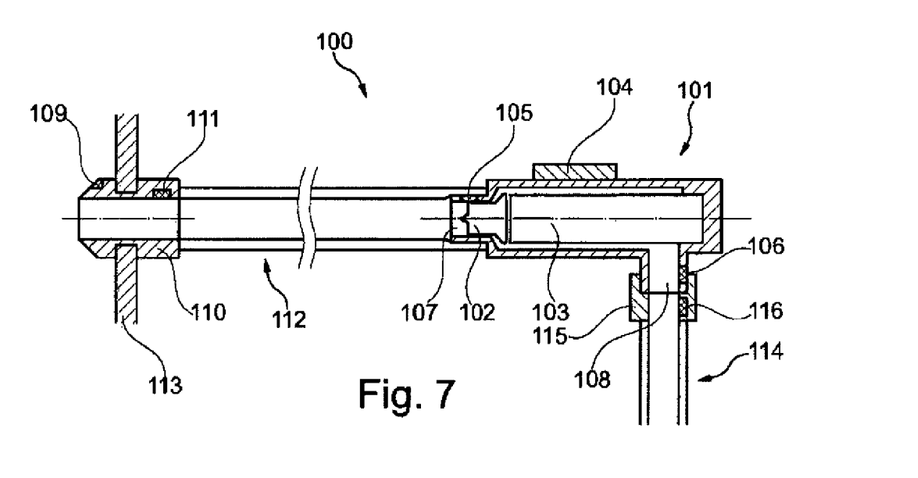

Also, combined flow and pressure measurement is possible, as is shown in the blood pump system 100 with the blood pump 101, shown in FIG. 7. Here the blood pump 101 with rotor 102 and motor 103 has a flow sensor 104 and pressure sensors 105, 106 at the pump inlet 107 and the pump outlet 108. In addition, also pressure sensors 109, 111 are provided at the tip 110 of the inlet cannula 112. Here, the pressure sensor 111 is placed on the inside of the tip 110 and thus measures the pressure at that point, whereas the pressure sensor 109 is distal to the heart wall 113 on the outside of the tip 110, and thus measures pressure in the atrium. In addition, the outlet cannula 114 at the outlet connector 115 includes a further pressure sensor 116, which determines the pressure at this point. There are sensors integrated in this system in the blood pump 101 at its inlet 107 and outlet 108, as well as in the tip 110 of the inlet cannula 112 and the outlet connector 115 of the outlet cannula 114. Thus there is at least one partial separation of the complex technical units of the pump 101 and the sensors. This minimises risk during production and during treatment switching of the pump 101 is not excluded. A change of the sensor technology is then only partially necessary.

Figure 8:
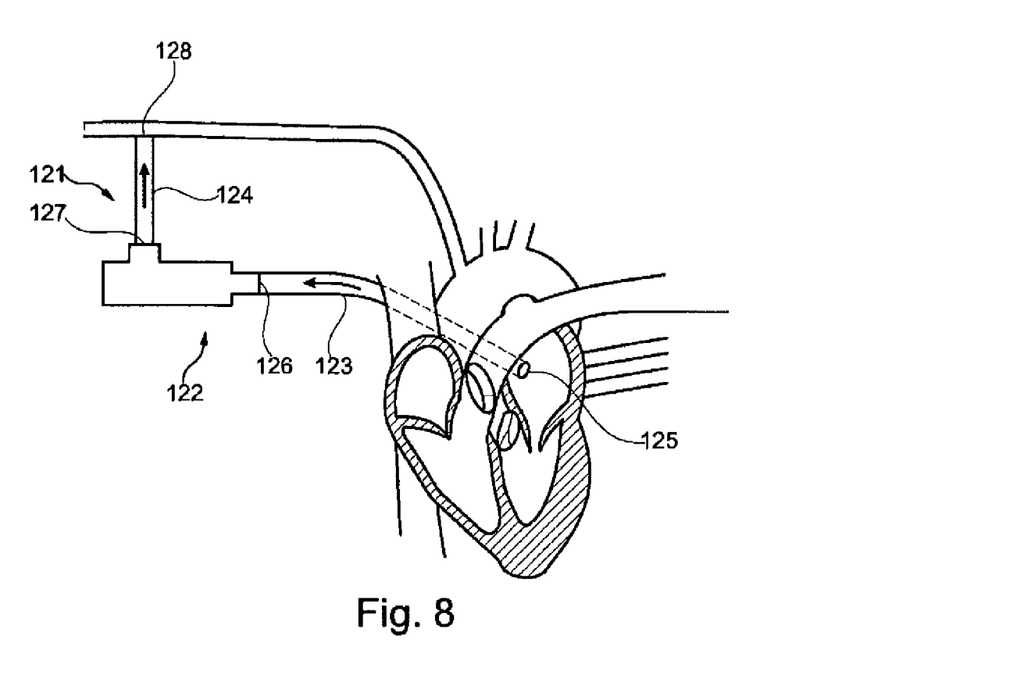
FIG. 8 a schematic representation of a blood pump in its operation location in the blood system between the atrium and arterial system, FIG. 9 a schematic representation of a system with a blood pump with an inlet and an outlet cannula with an outlet connector r with pressure measurement integrated into the pump inlet and outlet, here with integrated pressure measurement in the inlet cannula and an outlet connector as well as an integrated flow and temperature sensor technology, FIG. 10 a schematic representation of a blood pump in its operation location in the blood system between the ventricle and the arterial system, FIG. 11 a schematic representation of a blood pump at its operation location in the blood system between the ventricle and arterial system, whereby the pump inlet is placed directly without use of an intermediate cannula in the heart chamber, FIG. 12 a schematic representation of a blood pump on location in the blood system between the atrium and arterial system, whereby the pump inlet is directly placed without use of an intermediate cannula in the heart chamber, FIG. 13 a schematic view of a section of the tip of an inlet cannula and FIG. 14 a schematic representation of a cross-section of an outlet cannula with an outlet connector.

Altogether, such a system 121 measures the pressure at four places on the pump system 121 consisting of the blood pump 122, inlet cannula 123 and outlet cannula 124, as presented in the operating condition in the blood system in FIG. 8. Namely, the pressure directly in the atrium 125, the pressure at the pump inlet 126, the pressure at the pump outlet 127 and the pressure at entry to the aorta at the location 128. Thus the pressure at pump inlet 126 can be measured by in the blood pump 122 integrated sensors, as well as by a sensor integrated in the inside of the inlet cannula 123. Also the pressure at pump outlet 127 can be measured by a sensor integrated in the blood pump 122, as well as through a sensor integrated into the outlet sensor. Furthermore, the arrangement of a sensor at the tip of the outlet connector is also possible on the outside in order to measure aortal pressure.

Figure 9:
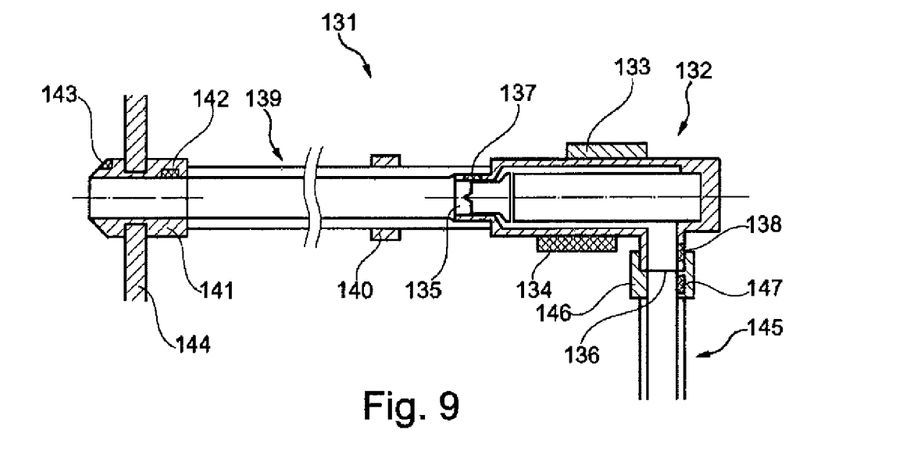

As shown in FIG. 9, one could also imagine a blood pump system 131 which unites all sensor types. Thus the blood pump 132 includes a flow sensor 133 as well as a temperature sensor 134. Furthermore, pressure sensors 137, 138 are integrated in the pump inlet 135 as well as in the pump outlet 136. The inlet cannula 139 also has a flow sensor 140. In addition, a pressure sensor 142 is integrated into a cannula tip 141 on the inside of the tip 141 and a pressure sensor 143 is provided on the outside of the tip 141 distal to the heart wall 144. In addition, the outlet cannula 145 in the outlet connector 146 has a pressure sensor 147. Thus, combined flow and pressure measurement is possible, which are both incorporated into the blood pump 132. and decoupled from the blood pump in the inlet cannula 139 and outlet cannula 145 at different locations.

Figure 10:
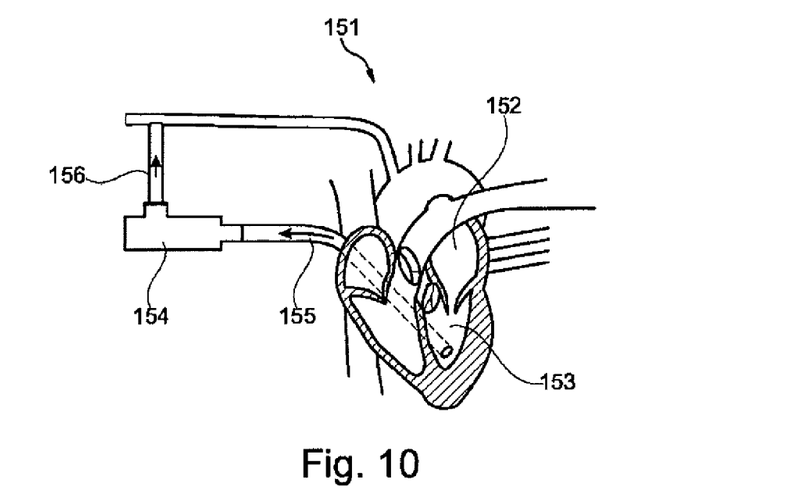

As an alternative to the location presented in FIG. 8 in the atrium 152, one can also implant directly into the ventricle 153. The blood pump system 151 consisting of blood pump 154 with inflow cannula 155 and outlet cannula 156 may then make the measurements by the appropriate sensors at the points indicated.

Figure 11:
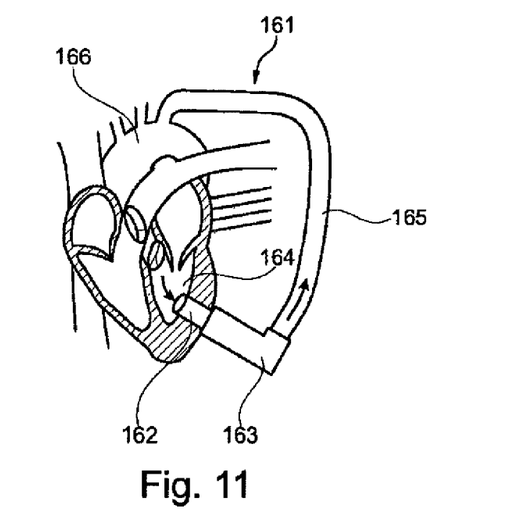
Figure 12:
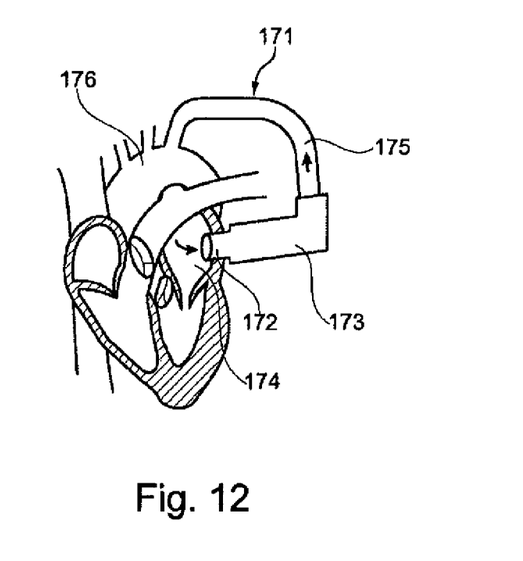

In addition, it is possible that one can place a pump system 161 or 171, as shown in FIGS. 11 and 12, so that the pump inlet 162, 172 of the blood pump 163, 173 can be placed directly into a heart chamber without interposition of a cannula, namely in the ventricle 164 or in the atrium 174. The outlet cannula 165, 175 is introduced into the aorta 166, 176. One of the sensors placed on the outside of the blood inlet 162, 172 (not pictured) can thus measure the chamber pressure. Also further flow and pressure sensors (not pictured) provide relevant data, such as pressure in the arterial system.

Figure 13:
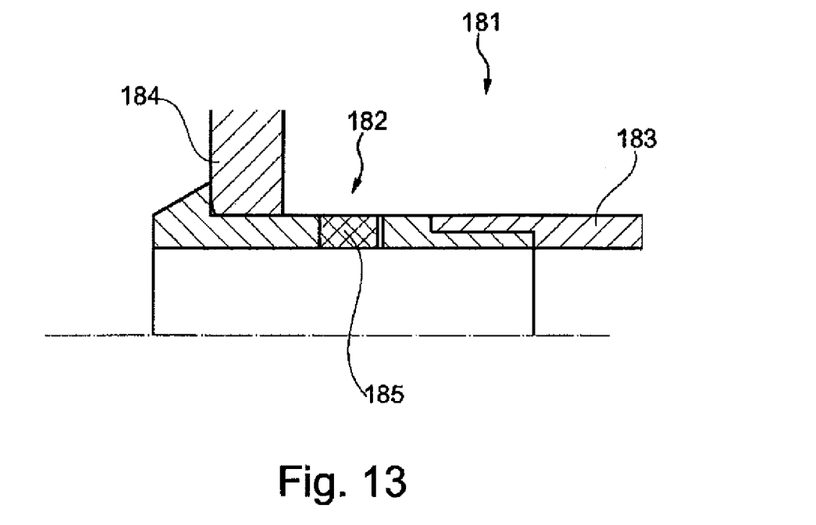

In detail, the inlet cannula 181, as is shown in FIG. 13, on the heart-facing side of the inlet cannula 181, has a tip 182 to which the cannula 183 is attached. The tip 182 is connected to the cannula 183 and engages at its tip with the heart wall 184. In addition, a pressure sensor 185 is integrated into the tip 182.

Figure 14:
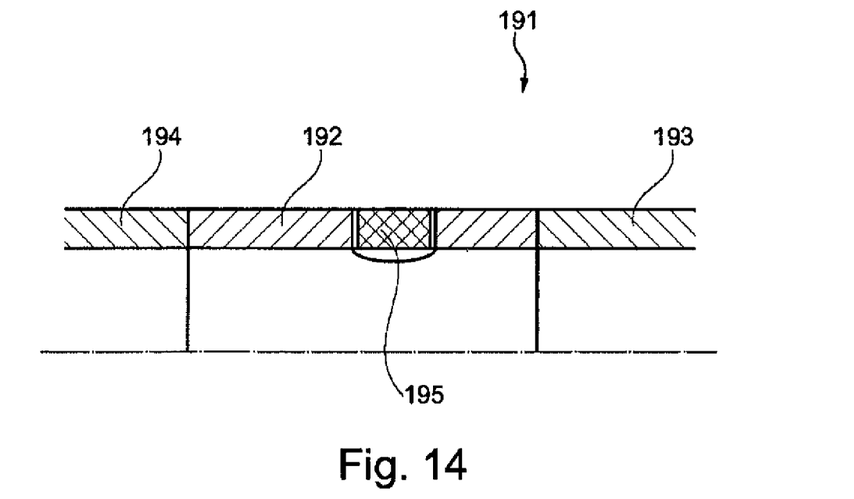

An outlet cannula 191, as shown in FIG. 14, has an outlet connector 192, over which the graft or the outlet 193 is connected to the blood pump 194. A pressure sensor 195 is integrated into the outlet connector 192.

The invention claimed is:

1. A blood pump comprising titanium and a measuring device to determine flow based on acoustic flow measurement processes, the measuring device including a measuring path with two coupling wedges with two transducers placed on these, the measuring device being attached to the blood pump such that an installation functions as a reflector.

2. The blood pump of claim 1, wherein the installation is a motor and that the flow is measured in an annular gap.

3. The blood pump of claim 1, wherein along the circumference, several measuring paths are arranged.

4. The blood pump of claim 3, wherein the measurement paths are placed on opposite sides.

5. The pump of claim 1, further comprising a sound wall arranged between the coupling wedges.

6. The blood pump of claim 1, wherein the measuring device is sealed hermetically in a space via the pump environment.

7. The blood pump of claim 6, further comprising a grommet arranged between the space and the inside of the pump.

8. The blood pump claim 7, wherein the grommet is arranged along the longitudinal axis.

9. The blood pump of claim 1, further comprising a temperature sensor.

10. The blood pump of claim 1, further comprising an integrated pressure sensor.

11. The blood pump of claim 10, wherein the pressure sensor is placed at a pump inlet and/or a pump outlet.

12. The blood pump of claim 10, which comprises a first pressure sensor and a second pressure sensor, wherein
 the first pressure sensor is arranged in such a way that it measures pressure in one heart chamber,
 and the second pressure sensor is arranged in such a way that it measures pressure in the downstream vascular system.

13. The system of claim 12, further comprising an outlet cannula with an outlet connector, wherein the outlet connector has a pressure sensor.

14. The system of claim 13, wherein the flow sensor is arranged at the outlet connector.

15. A system comprising the blood pump of claim 1, and an inlet cannula comprising a pressure sensor arranged at the tip of the inlet cannula.

16. The system of claim 15, wherein the pressure sensor is placed on the inside and/or the outside of the tip.

17. The system of claim 15, further comprising a flow sensor arranged at the inlet cannula.

18. A process for the preparation of the blood pump of claim 1, comprising cutting the coupling wedges from a pump housing.

19. The process of claim 18, wherein a wall which encloses one of the coupling wedges is milled from the pump housing.

20. The process of claim 19, wherein a drill hole is drilled from inside the wall to the interior of the pump.

21. The process of claim 20, wherein the drill hole is drilled in an axial direction.

22. The process of claim 19, further comprising placing a cover on the wall, so that coupling wedges are hermetically sealed from the pump environment.

23. The process of claim 22, wherein the cover is welded to the wall.

* * * * *